United States Patent [19]

Debourge et al.

[11] 4,058,600

[45] Nov. 15, 1977

[54] FUNGICIDAL TREATMENT AND COMPOSITION

[75] Inventors: Jean-Claude Debourge, Courbevoie; Martine Trochme, Lyon, both of France

[73] Assignee: Philagro S.A., France

[21] Appl. No.: 681,116

[22] Filed: Apr. 28, 1976

[51] Int. Cl.$^2$ .............................................. A01N 11/00
[52] U.S. Cl. .................................................... 424/128
[58] Field of Search .......................................... 424/128

[56] References Cited

U.S. PATENT DOCUMENTS

| | | | |
|---|---|---|---|
| 2,773,796 | 12/1956 | Hackmann et al. | 424/128 |
| 3,414,390 | 12/1968 | Riess et al. | 424/128 |
| 3,535,331 | 10/1970 | Glamkowski | 260/302 |

FOREIGN PATENT DOCUMENTS

| | | | |
|---|---|---|---|
| 2,119,882 | 11/1972 | France | 424/128 |

*Primary Examiner*—Albert T. Meyers
*Assistant Examiner*—D. W. Robinson
*Attorney, Agent, or Firm*—Robert E. Burns; Emmanuel J. Lobato; Bruce L. Adams

[57] ABSTRACT

A method of treating and protecting plants from fungal infections by topical and systemic application with hypophosphites is described. The hypophosphites are selected from the group consisting of hypophosphorous acid ($H_3PO_2$) and its salts with monovalent, and multivalent inorganic ions.

16 Claims, No Drawings

FUNGICIDAL TREATMENT AND COMPOSITION

FIELD OF THE INVENTION

This invention relates to fungicidal method and compositions based on hypophosphorous acid or its salts.

More particularly, the invention relates to compositions which may be used in controlling parasitic fungi in plants and which contain as active material at least one compound selected from the group comprising hypophosphorous acid and its mineral salts.

Examples of these salts include the hypophosphorous salts of alkalis, such as ammonium or sodium, lithium, potassium, the salts of alkaline earth metals, such as magnesium, calcium, barium or strontium, or the salts of heavier metals such as copper, iron, nickel, manganese, zinc or aluminium. All the salts are in anhydrous and/or more or less hydrated form.

BACKGROUND

These compounds are known per se (cf. in particular Nouveau Traite de Chimie Minerale by Paul PASCAL, published by Masson), and the majority are even commercially available products which may be used as starting materials for producing other salts by conventional processes, such as by more or less heavy neutralisation of the acid or double decomposition. Hypophosphorous acid and some of its salts are soluble in water, whilst other salts are insoluble in water.

Although certain organophosphorous compounds, especially phosphites, have been proposed as active fungicidal materials, the literature does not describe the fungicidal properties of hypophosphites.

THE INVENTION

It has now been found that the compounds according to the invention have excellent fungicidal properties and that they may be used with advantage as active materials in compositions for protecting plants against fungous diseases. The following compounds were tested:
1. Commercial-grade hypophosphorous acid in the form of a 60 % aqueous solution, density 1.26.
2. Ammonium hypophosphite $(NH_4)H_2PO_2$, melting point 100° C.
3. Sodium hypophosphite: $NaH_2PO_2.H_2O$, pure commercial-grade.
4. Potassium hypophosphite: $KH_2PO_2$, pure commercial-grade.
5. Calcium hypophosphite: $Ca(H_2PO_2)_2$, pure commercial-grade.
6. Magnesium hypophosphite: $Mg(H_2PO_2)_2 \cdot 6H_2O$, pure commercial-grade.
7. Barium hypophosphite: $Ba(H_2PO_2)_2$, chemically pure, commercial-grade, soluble in water.
8. Manganese (II) hypophosphite: $Mn(H_2PO_2)_2H_2O$ commercial-grade.
9. Iron (I II) hypophosphite: $Fe(H_2PO_2)_3$, pure commercial-grade.

DETAILED DESCRIPTION

The fungicidal properties of the compounds according to the invention are various, although they are particularly the following Examples.

EXAMPLE 1:

In vitro test on mycelian growth

The compounds according to the invention are tested for their action on the mycelian growth of the following fungi:
- Pythium de Baryanum (phycomycetes), responsible for the damping-off of seedlings,
- Rhizoctonia solani (basidiomycetes), responsible for foot rot,
- Botrytis cinerea (ascomycetes), responsible for grey mold,
- Septoria apii (Fungi imperfecti), responsible for leaf spot in celery.

The agar plate dilution method is used for each test. A mixture of 5 cc of gelose and 0.5 cc of an acetone solution or of a wettable powder containing the material to be tested in a concentration of 1 g/l is poured into a test tube at a temperature of approximately 50° C.

The wettable powder is prepared by mixing the following ingredients for 1 minute in a rotary cutter blender:

| | |
|---|---|
| active material to be tested | 20% |
| deflocculant (calcium lignosulphate) | 5% |
| wetting agent (sodium alkylaryl sulphate) | 1% |
| filler (aluminium silicate) | 74% |

This wettable powder is then mixed with a quantity of water sufficient for one application in the required dose.

The gelose-containing mixture is left to harden and mycelian growth discs of the fungus are placed on it.

A Petri dish similar to the preceding Petri dish, except that its gelose medium does not contain any active material, is used as control.

After 4 days at 20° C, the surface area of the inhibition zone observed is evaluated and expressed as a percentage in relation to the inoculated surface.

Under these conditions, it is found that compound No. 2 gives a percentage inhibition of Botrytis cinerea and Septoria apii of 51% and 62%, respectively, and that compound No. 5 gives a percentage inhibition of Pythium de Baryanum and Rhizoctonia solani of 77% and 48%, respectively.

EXAMPLE 2:

In vivo test on Plasmopara viticola (phycomycetes family) in grape vine plants a. Preventive treatment Using a spray gun, the leaves of pot-grown vine plants (Gamay variety) were sprayed underneath, until dripping wet, with an aqueous suspension of a wettable powder having the following composition (by weight):

| | |
|---|---|
| active material to be tested | 20% |
| deflocculant (calcium lignosulphate) | 5% |
| wetting agent (sodium alkylarly sulphonate) | 1% |
| filler (aluminium silicate) | 74% |

This suspension was diluted to the required extent and contains the active material to be tested in the desired dose. Each test was replicated three times.

After 48 hours, the plants were infected by spraying the leaves underneath with an aqueous suspension containing approximately 80,000 units/cc of spores of the fungus.

The pots were then stored for 48 hours in an incubation cell at 20° C/100% relative humidity.

The plants were inspected 9 days after infestation.

Under these conditions, it was found that, in a dose of 0.5 g/l, compounds Nos. 1, 2, 4, 6 and 7 afford good protection and that, in a dose of 1 gll, compounds Nos. 3, 5 and 8 afford good protection.

In addition, it was found that none of the compounds tested showed the least sign of phytotoxicity.

b. Systemic test by root absorption

Several vine stocks (Gamay variety) each accommodated in a container filled with vermiculite and a nutritive solution, were sprayed with 40 cc of a 0.5 g/l solution of the material to be tested. After 2 days, the vine stocks were infected with an aqueous suspension containing 100,000 spores/cc of *Plasmopara viticola*. This was followed by incubation for 48 hours in a room at 20° C/100% relative humidity. The degree of infestation was assessed after about 9 days relative to an infested control which had been sprayed with 40 cc of distilled water.

Under these conditions, it was found that, in this dose of 0.5 g/l, compounds Nos. 1, 2, 3, 4, 7 and 9, which are absorbed by the roots, provided the vine leaves with complete protection against mildew, which clearly demonstrates the systemic nature of these compounds.

c. Systemic test after contamination

Several vine stocks (Gamay variety), each accommodated in a container filled with vermiculite and a nutritive solution, are contaminated with 40 cc/plant of an aqueous suspension containing 100,000 spores/cc of *Plasmopara viticola*. This is followed by incubation for 48 hours in a room at 20° C/100% relative humidity.

After 2 days, the plants are sprayed with 40 cc/plant of a solution containing 2.5 g/l of the active material to be tested.

The degree of infestation was assessed after about 9 days in relation to an infested control which had been sprayed with 40 cc of distilled water.

Under these conditions, it was found that, in this dose of 2.5 g/l, compound No. 6 affords the vine leaves complete protection whilst compounds Nos. 5, 8 and 9 afford them good protection against mildew, which clearly demonstrates the systemic nature of these compounds.

These Examples clearly illustrate the preventive and systemic fungicidal activity of the compounds according to the invention on fungi belonging to the phycomycetes, basidiomycetes, ascomycetes and Fungi imperfecti families, and in particular their remarkable activity on mildew of the vine. In addition, some of the compounds according to the invention are effective against other mildews, especially in tobacco, *Peronospora tabacina*, and in hops, *Peronospora humili*, and against various parasitic Phytophtora in plants grown in temperate or tropical climates.

Accordingly, these compounds are particularly suitable for use in the preventive or curative treatment of parasitic fungi in plants belonging to the above-mentioned families.

It has also been found that these compounds may be mixed with other phosphorus derivatives of the type used as antimildew fungicides, more especially the 2-hydroxy-1,3,2-di- oxaphospholanes, the β-hydroxy ethyl phosphites, phosphorous acid and its salts, the phosphonic monoesters and diesters, the cyclic diphosphorus compounds, the aminophosphites, the 2-hydroxy-1,3,2-dioxaphosphorinanes and the γ-hydroxy propyl phosphites, the phosphorus-based trialkyl imides, the 2H-2-thio-1,3,2-dioxaphospholanes and phosphorinanes and the thio(alkyl)phosphites which are respectively the subjects of French Patent Applications Nos. 73-01.803, 73-37.994, 73-43.081, 73-45.627, 74-08.995, 74-10.988, 74-13.246, 74-34.529, 74-34.530 in the name of PEPRO S.A. 75-04.394 and 75-08.642 in the name of PHILAGRO S.A.

The doses in which the compounds are used may vary within wide limits according to the virulence of the fungus and the climatic conditions. Generally, doses of from 0.01 to 5 g/l of active material are entirely adequate.

For their practical application, the compounds according to the invention are rarely used on their own. In most cases, they form part of formulations which generally contain a carrier and/or a surface-active agent in addition to the active material according to the invention.

In the context of the invention, a "carrier" is an organic or inorganic, natural or synthetic material with which the active material is associated so as to facilitate its application to the plant, to seeds or to the soil, or to facilitate its transport or its handling. The carrier may be solid (clays, natural or synthetic silicates, resins, waxes, solid fertilisers) or fluid (water, alcohols, ketones, petroleum fractions, chlorinated hydrocarbons, liquefied gases).

The surface-active agent may be an ionic or non-ionic emulsifying, dispersing or wetting agent, for example salts of polyacrylic acids and of lignin sulphonic acids, condensates of ethylene oxide with fatty alcohols, fatty acids or fatty amines.

The compositions according to the invention can be prepared in the form of wettable powders, soluble powders, dusting powders, granules, solutions, emulsifiable concentrates, emulsions, suspension concentrates and aerosols.

The wettable powders are normally prepared in such a way that they contain from 20 to 95% by weight of active material, and normally contain, in addition to a solid carrier, from 0 to 5% by weight of a wetting agent, from 3 to 10% by weight of a dispersing agent and, when necessary, from 0 to 10% by weight of one or more stabilisers and/or other additives, such as penetrating agents, adhesives or anti-caking agents, dyestuffs, etc. The composition of a wettable powder is given by way of example in the following:

| | |
|---|---|
| active material | 50% |
| calcium lignosulphate (deflocculant) | 5% |
| anionic wetting agent | 1% |
| anticaking silica | 5% |
| kaolin (filler) | 39% |

The water-soluble powders are obtained by mixing from 20 to 95% by weight of active material, from 0 to 10% of an anticaking filler and from 0 to 1% of a wetting agent, the rest being made up by a water soluble filler, primarily a salt.

One example of the composition of a water-soluble powder is given below:

| | |
|---|---|
| active material | 70% |
| anionic wetting agent | 0.5% |
| anticaking silica | 5% |
| sodium sulphate (soluble filler) | 24.5% |

Aqueous dispersions and emulsions, for example compositions obtained by diluting with water a wettable powder or an emulsifiable concentrate according to the invention, are included within the general scope of the present invention. These emulsions may be of the water-in-oil type or of the oil-in-water type and they may have a thick consistency resembling that of a "mayonnaise".

The compositions according to the invention may contain other ingredients, for example protective colloids, adhesives or thickeners, thixotropic agents, stabilisers or sequestrants and other active materials known to have useful agricultural pesticidal properties, especially acaricides or insecticides.

We claim:

1. A fungicidal composition for use in controlling fungus disease in plants, containing a fungicidally effective amount of hypophophorous acid or its mineral salts in an agriculturally acceptable vehicle suitable for topical application.

2. The composition of claim 1, containing an alkali hypophosphite.

3. The composition of claim 2, containing ammonium hypophosphite.

4. The composition of claim 1, containing an alkaline earth hypophosphite.

5. The composition of claim 4, containing calcium hypophosphite.

6. The composition of claim 4, containing magnesium hypophosphite.

7. The composition of claim 1, containing a hypophosphite of a metal selected from the group consisting of iron, copper, nickel, manganese, zinc and aluminium.

8. The fungicidal composition of claim 1 wherein said mineral hypophosphite comprises 20 to 95wt % of said composition and said vehicle includes a carrier for said active material and a surfactant.

9. The composition of claim 8 wherein said composition is a wettable powder.

10. The composition of claim 8 wherein said composition is a water-soluble powder.

11. A process for the preventive or curative treatment of plants against fungus disease which comprises applying to said plants or to the environs thereof, a fungicidal amount of hypophosphorus acid or its mineral salts in an agriculturally acceptable vehicle 12. The process of claim 11, wherein the plants are treated against fungi belonging to the phycomycetes family.

13. The process of claim 12, wherein said plant is grape-vine and is treated against mildew.

14. The process of claim 11, wherein the plants are treated against fungi belonging to the ascomycetes family.

15. The process of claim 11, wherein the plants are treated against fungi belonging to the basidiomycetes family.

16. The process of claim 11, wherein the plants are treated against fungi belonging to the Fungi imperfecti family.

* * * * *